US00PP28952P2

(12) United States Plant Patent
Bol

(10) Patent No.: US PP28,952 P2
(45) Date of Patent: Feb. 6, 2018

(54) ***ECHINACEA* PLANT NAMED 'TWEETY'**

(50) Latin Name: ***Echinacea* hybrid**
Varietal Denomination: Tweety

(71) Applicant: Derrick Cornelis Bol, Valkenburg (NL)

(72) Inventor: Derrick Cornelis Bol, Valkenburg (NL)

( * ) Notice: Subject to any disclaimer, the term of this patent is extended or adjusted under 35 U.S.C. 154(b) by 0 days.

(21) Appl. No.: 15/530,314

(22) Filed: Dec. 21, 2016

(51) Int. Cl.
*A01H 5/02* (2006.01)

(52) U.S. Cl.
USPC ..... Plt./428

(58) Field of Classification Search
USPC ..... Plt./428
CPC ..... A01H 5/025
See application file for complete search history.

*Primary Examiner* — Kent L Bell
(74) *Attorney, Agent, or Firm* — Penny J. Aguirre

(57) ABSTRACT

A new cultivar of hybrid *Echinacea* named 'Tweety' characterized by its very compact plant habit, its inflorescences with ray florets that are orange-yellow in color and elliptic in shape surrounding bright orange disk florets, and its strong flowering stems.

2 Drawing Sheets

Botanical classification: *Echinacea* hybrid.
Variety denomination: 'Tweety'.

BACKGROUND OF THE INVENTION

The present invention relates to a new and distinct cultivar of *Echinacea* of hybrid origin and will be referred to hereafter by its cultivar name 'Tweety'. 'Tweety' is an herbaceous perennial grown for landscape and container use.

The new invention arose from an ongoing controlled breeding program in Woerden, The Netherlands. The objective of the breeding program is to develop cultivars of *Echinacea* with unique flowers and compact plant habits.

The Inventor made controlled crosses in summer of 2011 in his test garden between unnamed and unpatented proprietary seedlings with compact plant habits as both the female and male parents. The seeds were pooled from the crosses before sowing and the exact parents are unknown. 'Tweety' was selected in summer of 2012 as a single unique plant amongst the resulting seedlings from the above crosses.

Asexual propagation of the new cultivar was first accomplished by division in Woerden, The Netherlands in 2012 by the Inventor. Asexual propagation by tissue culture using meristem tissue and division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Tweety' as unique cultivar of *Echinacea*.

1. 'Tweety' exhibits a very compact plant habit.
2. 'Tweety' exhibits inflorescences with ray florets that are orange-yellow in color and elliptic in shape surrounding orange disc florets.
3. 'Tweety' exhibits strong flowering stems.

'Tweety' can be most closely compared to the *Echinacea* cultivars 'Dixie Star', (U.S. Plant Pat. No. 26,160) and 'Chiquita' (U.S. Plant Pat. No. 24,505). Both 'Dixie Star' and 'Chiquita' are similar to 'Tweety' in having compact plant habits. 'Dixie Star' differs from 'Tweety' in having a less compact plant habit and in having inflorescences with ray florets that open orange-yellow and change to yellow. 'Chiquita' differs from 'Tweety' in having a less compact plant habit and in having inflorescences with ray florets that are pale yellow in color.

BRIEF DESCRIPTION OF THE DRAWINGS

The accompanying colored photographs illustrate the overall appearance and distinct characteristics of the new *Echinacea*. The photographs were taken of six month-old plants of the new cultivar as field grown in Woerden, The Netherlands (placed in a 21-cm container for the photographs).

The photograph in FIG. 1 illustrates the overall habit and appearance of 'Tweety' in bloom.

Figure 1:
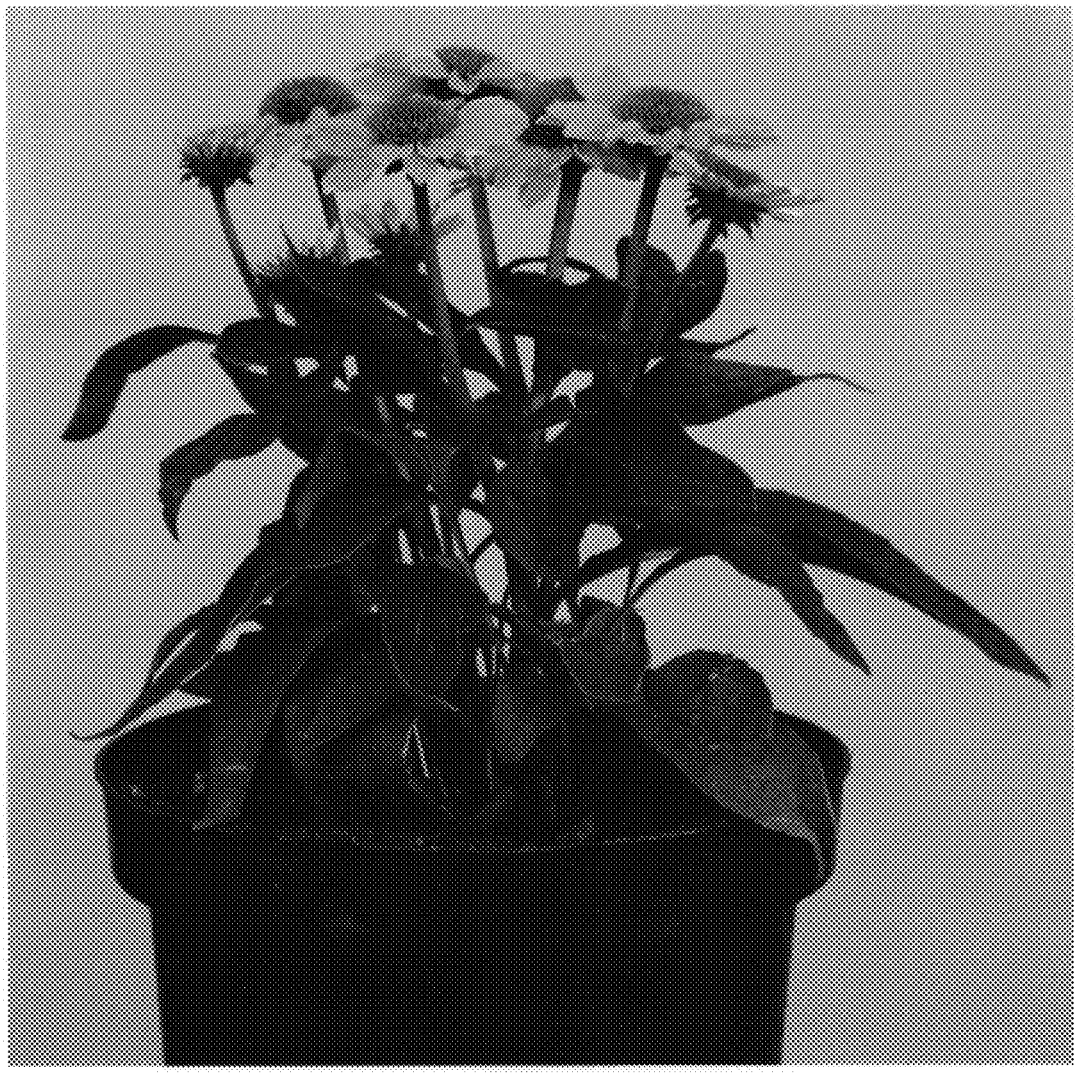
Figure 2:
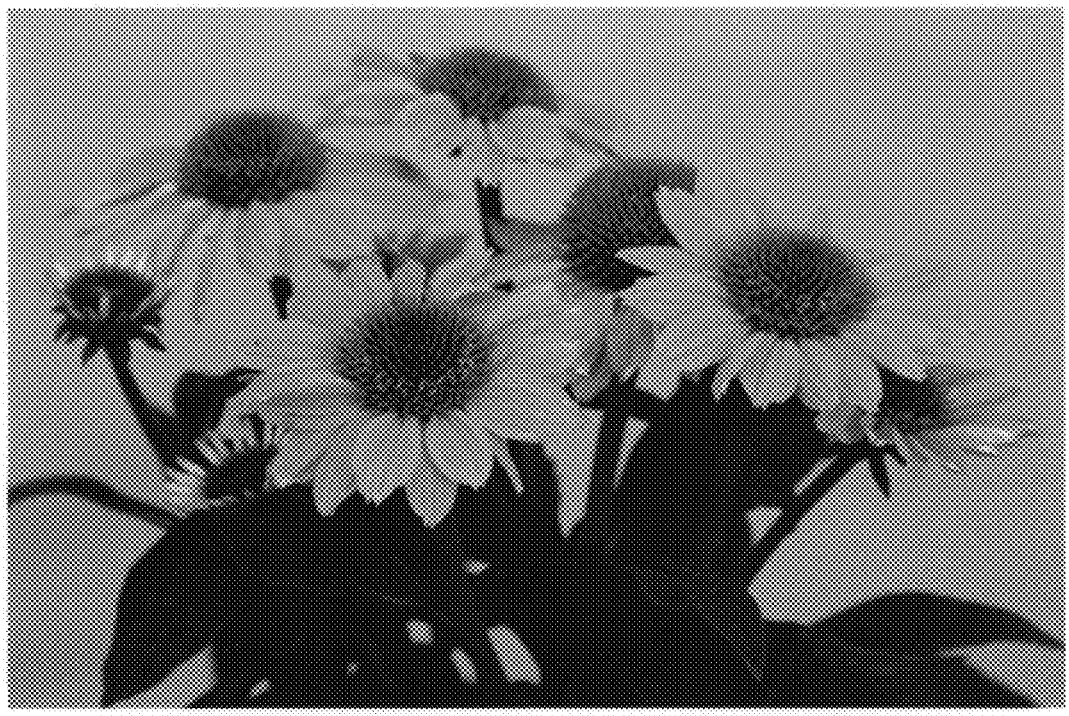

The photograph in FIG. 2 provides a close-up view of the inflorescences of 'Tweety'.

Figure 3:
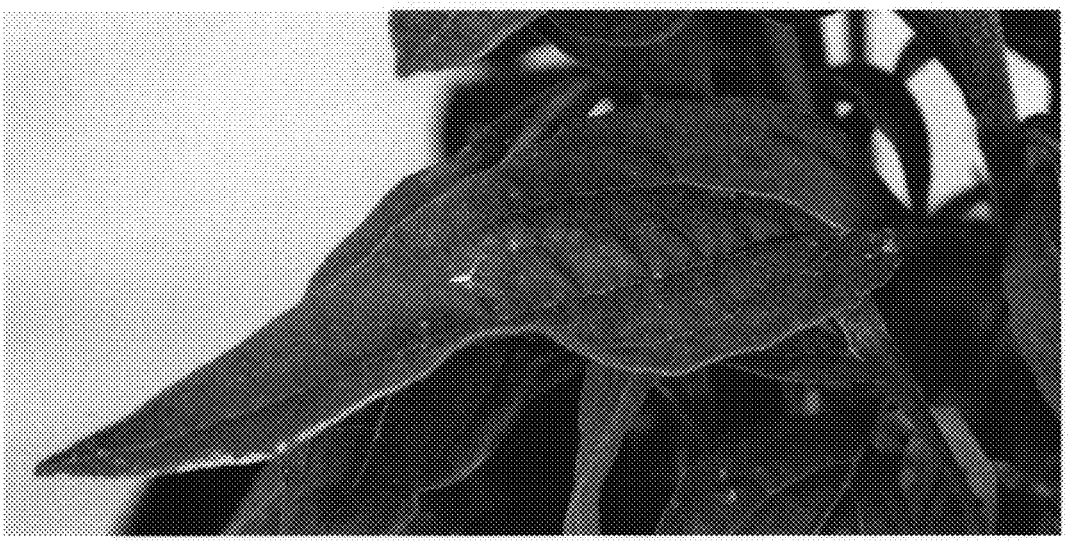

The photograph in FIG. 3 provides a close-up view of a leaf of 'Tweety'.

The colors in the photographs are as close as possible with the photographic and printing technology utilized and color values cited in the detailed botanical description accurately describe the colors of the new *Echinacea*.

DETAILED BOTANICAL DESCRIPTION

The following is a detailed description of six month-old plants of the new cultivar as field grown in Woerden, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Blooms from early July to late September, in Woerden, The Netherlands.

*Plant type.*—Herbaceous perennial.

*Plant habit.*—Very compact, broad upright.

*Height and spread.*—An average of 21.6 cm (including inflorescences) and an average of 31 cm in spread.

*Cold hardiness.*—U.S.D.A Zones 3 to 10.

*Diseases resistance.*—Similar susceptibility and resistance to diseases and pests as other *Echinacea* varieties.

*Root description.*—Fibrous and fine, 158D in color.

*Propagation.*—Tissue culture using meristem tissue and division.

*Growth rate.*—Moderate.

*Root development.*—A young rooted plant can be produced in about 3 months.

Stem description:

*Shape.*—Rounded.

*Stem color.*—Young branches; 143C, mature branches; 143A.

*Stem size.*—An average of 10 cm in length, 4 mm in diameter.

*Stem strength.*—Strong.

*Stem aspect.*—Primary branches grow in an average angle of 5° to vertical stems (0°=horizontal), secondary branches grow in an average angle of 30° to primary branches.

*Stem surface.*—Moderately glossy and moderately rough to touch, densely covered with short strigose hairs average of 0.5 mm in length and NN155A in color.

*Stem number.*—Average of 4 primary branches and 1 secondary branch per main branch.

*Internode length.*—Average of 2.6 cm in length, 143A in color.

*Branching.*—Main flowering stem grows from base.

Foliage description:

*Leaf shape.*—Ovate to narrow ovate.

*Leaf division.*—Simple.

*Leaf base.*—Attenuate to short attenuate.

*Leaf apex.*—Acute.

*Leaf venation.*—Pinnate, upper and lower surface 145A in color.

*Leaf margins.*—Entire to shallowly dentate.

*Leaf attachment.*—Petiolate.

*Leaf arrangement.*—Alternate.

*Leaf size.*—Average of 12.8 cm in length and 4.4 cm in width.

*Leaf color.*—Young upper surface; 137B to 137C, young lower surface; between 137C and 138A, mature upper surface; NN137A, mature lower surface; NN137C to NN137D.

*Leaf surface.*—Upper and lower surfaces are matte, rough to the touch due to pubescence and densely covered with short strigose hairs an average of 0.5 mm in length and NN155A in color.

*Petioles.*—U-shaped, 4 cm in length and 3 mm in diameter, color upper surface 144B to 144C, color lower surface 144B, both surfaces glossy and covered with short strigose hairs; an average length is 0.3 mm and NN155B in color.

Flower description:

*Type.*—Terminal capitulum consisting of ray florets and disc florets.

*Capitulum number.*—An average of 1 per stem, 9 per plant.

*Lastingness of inflorescence.*—Average of 2 weeks, ray florets self-cleaning.

*Capitulum size.*—Matures to about 2.7 cm in height and 7.6 cm in diameter, disc diameter is an average of 3.2 cm and disc height is an average of 6 mm.

*Fragrance.*—Slightly to moderately fragrant and pleasant.

*Involucral bracts or phyllary.*—Rotate, 70 arranged in 3 overlapping rows, average of 7 mm in length and 3 mm in width, broad cuneate base, acute apex, ovate in shape, color upper surface NN137A, color lower surface NN137B, upper surface texture; glabrous and slightly glossy, lower surface texture; matte and moderately pubescent with very short strigose hairs an average of 0.3 mm in length and NN155A in color, margins are entire and moderately pubescent with very short strigose hairs, an average of 0.3 mm in length and NN155A in color.

*Buds.*—Inverted triangle in shape, an average of 1.8 cm in length and 2.6 cm in diameter, 8C in color, matte surface texture.

*Peduncle.*—Strong, terminal is an average of 7.1 cm in length, 4 mm in diameter, upright aspect, 143A in color, surface is moderately glossy and densely covered with short strigose hairs, 0.5 mm in length and NN155A in color.

*Ray florets.*—Rotate around disc in 1 row, average of 22 per inflorescence, elliptic in shape, average of 3 cm in length and 1.2 cm in width, emarginate to praemorse apex, cuneate base, entire margin, outward, slightly drooping in an average angle of −10° downward from horizontal, color; upper surface when opening 17B to 17C, lower surface when opening 18C, upper surface when fully open 23A, lower surface when fully open 20D, tip 149A to 149B, upper surface fading to between 21A and 23A, lower surface fading to 11C, tip 144C, surface texture; upper surface glabrous, moderately velvety and matte, lower surface glabrous, slightly velvety and slightly to moderately glossy.

*Disc flowers (bisexual).*—Numerous, average of 300, arranged spirally on disc in 12 rows, tubular appearance, upright to outward aspect, apex is acute on upper 16% that is free, fused (tubular) base, entire margin, average of 1 cm in length and 2 mm in width, upper and lower surface textures are glabrous and glossy, color; when opening upper and lower surface 143C, mid-section and base 145C, when fully open upper and lower surface 144A, mid-section and base 145C.

*Disc spines.*—Average of 400, acicular in shape, narrow acute apex, cuneate base, smooth, glabrous and glossy surface, color is 17A at apex, 143B in mid region and 145D at base.

*Receptacle.*—Triangular in shape, an average of 6 mm in height and diameter, and 157D in color.

Reproductive organs (present on disc florets only):

*Gynoecium.*—Pistil; 1, 7 mm in length, style; 5.5 mm in length and 145C in color, stigma; cleft, decurrent and 151C to 151D in color, ovary; 145D in color.

*Androecium.*—Stamens; 5, filaments; 3 mm in length and 145D in color, anthers; narrow oblong in shape, 2.5 mm in length, 0.5 mm in width and N200A to N200B in color, pollen is moderate in quantity and 17A in color.

*Fruit/seed.*—No seed production has been observed.

It is claimed:

1. A new and distinct cultivar of *Echinacea* plant named 'Tweety' as herein illustrated and described.

* * * * *